(12) United States Patent
Beaupre (10) Patent No.: US 6,752,815 B2
(45) Date of Patent: Jun. 22, 2004

(54) METHOD AND WAVEGUIDES FOR CHANGING THE DIRECTION OF LONGITUDINAL VIBRATIONS

(75) Inventor: Jean M. Beaupre, Blue Ash, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 537 days.

(21) Appl. No.: 09/774,907

(22) Filed: Jan. 31, 2001

(65) Prior Publication Data

US 2002/0128674 A1 Sep. 12, 2002

(51) Int. Cl.⁷ .................................................. A61B 17/32
(52) U.S. Cl. ........................................ 606/169; 604/22
(58) Field of Search ................................. 606/169, 167, 606/170, 171; 604/22

(56) References Cited

U.S. PATENT DOCUMENTS

| | | | | |
|---|---|---|---|---|
| 4,561,438 A | * | 12/1985 | Bonnet et al. | 606/128 |
| 4,974,581 A | * | 12/1990 | Wiksell | 601/2 |
| 5,222,937 A | * | 6/1993 | Kagawa | 604/22 |
| 5,531,597 A | * | 7/1996 | Foulkes et al. | 433/119 |
| 5,653,724 A | * | 8/1997 | Imonti | 606/169 |
| 5,669,922 A | * | 9/1997 | Hood | 606/169 |
| 5,725,370 A | * | 3/1998 | Himeno et al. | 433/86 |
| 5,772,434 A | * | 6/1998 | Winston | 433/119 |
| 5,897,523 A | | 4/1999 | Wright et al. | |
| 6,063,098 A | | 5/2000 | Houser et al. | |
| 6,312,256 B1 | * | 11/2001 | Dieras et al. | 433/119 |
| 6,325,811 B1 | * | 12/2001 | Messerly | 606/169 |
| 2001/0027325 A1 | * | 10/2001 | Beaupre | 606/169 |
| 2002/0156493 A1 | * | 10/2002 | Houser et al. | 606/169 |

OTHER PUBLICATIONS

S.N. Makarov, et al., "The Longitudinal Vibration Response of a Curved Fiber Used for Laser Ultrasound Surgical Therapy", J. Acoust Soc. Am. vol. 102 No. 2, Pt. 1. Aug. 1997, pp. 1191–1199.

* cited by examiner

Primary Examiner—Henry Bennett
Assistant Examiner—Kathryn Odland (57) ABSTRACT

A curved ultrasonic waveguide, as used in an ultrasonic surgical instrument, includes two curved half-wave sections, having similar vibratory motion at their respective distal tips, which are integrally or compressively joined at the distal tips to create a single waveguide with a sharper bend radius than is conventionally possible. The resulting waveguide does not produce parasitic motion or generate excessive heat at the input or output portions of the waveguide.

20 Claims, 8 Drawing Sheets

PRIOR ART

METHOD AND WAVEGUIDES FOR CHANGING THE DIRECTION OF LONGITUDINAL VIBRATIONS

BACKGROUND OF THE INVENTION

1. Field of the Invention

The present invention relates generally to a method and waveguides for changing the direction of longitudinal vibrations, and more particularly pertains to a method and waveguides for changing the direction of longitudinal vibrations which maintain efficiency of operation over a larger angle of change than prior art designers typically accepted as possible.

2. Discussion of the Prior Art

In the design of acoustic or electromagnetic waveguides it is widely believed that sharp turns in a waveguide lead to inefficiencies of parasitic motion, excessive heat generation and noise. A common rule of thumb holds that a radius of curvature of a waveguide should not be less than the transmitted wavelength because a smaller radius of curvature causes the efficiency of the waveguide to quickly drop below 100%. A cutoff radius occurs at approximately one-sixth the wavelength. Designers define a cutoff radius R by the equation $R > \lambda/2\pi$, where $\lambda$ represents the wavelength of the transmitted energy and $\pi$ is the well-known ratio of the circumference of any circle to its diameter, or approximately 3.14.

Prior art waveguide designs avoided having a radius of curvature less than the cutoff radius because the efficiency of the waveguide can diminish below 50%. The waveguide loses efficiency regardless of the angle of the bend. Any bend in prior art waveguides can induce parasitic motion which can produce heat and noise, and result in reduced component life, especially if the radius of the waveguide itself is greater than ten percent of the waveguide's radius of curvature.

In the prior art, redirecting longitudinal motion was typically performed by either bending the waveguide, usually in a continuous curve, to the degree desired, or by exciting subharmonics and deriving use from the subharmonics. Both methods produce a superposition of motions that propagate both proximal and distal to the bend. The component of the motion not parallel to the longitudinal axis of the waveguide produces heat and noise, and can destroy the device at high powers.

SUMMARY OF THE INVENTION

Accordingly, it is a primary object of the present invention to provide a method and waveguides for changing the direction of longitudinal vibrations.

The present invention redirects substantially longitudinal motion along a first axis to substantially longitudinal motion along a second axis inclined at an angle relative to the first axis much more efficiently than prior art devices. The present invention maintains efficiency even when the waveguide has a very tight radius of curvature in the section between the two axes, and maintains efficiency over a larger angle than prior art designers typically accepted as possible without any reduction in utility. When a waveguide pursuant to the present invention redirects longitudinal motion over reduced angles similar to those used in the prior art, higher efficiencies are obtained than with conventional prior art designs. Moreover, analysis has shown that angles up to the maximum possible angle of 180 degrees can be achieved with the present invention with no restrictions on the radii of curvature. The present invention can result in transmission efficiencies near 100% at all angles even when the radius of the waveguide exceeds 10% of the waveguide's radius of curvature. Contradicting current theory, the novel waveguide designs benefit from smaller radii of curvature, especially at larger bend angles.

The waveguides of the present invention comprise first and second half-wave sections, each having a straight portion, a curved portion and a balancing region. The half-wave sections join into one continuous piece, or are compressively loaded against each other, at the tips of their curved portions. The vibrations at the tip of the curved portion of the first half-wave section are substantially identical in magnitude and direction to the vibrations at the tip of the curved portion of the second half-wave section. The direction of vibration at the tip of each respective curved portion of each section is preferably tangential to the curve, but the present invention does not require that limitation.

In a simple embodiment, the present invention comprises two identical half-wave sections joined at the tips of their curved portions. Alternative embodiments can encompass any geometry on either half-wave section, not necessarily identical, as long as the direction of vibration of the tip of each section is substantially identical.

Slightly modifying the existing balancing features would require minor tuning to correct for higher order effects (such as a nonuniform velocity profile along the joining surfaces). The slight modification entails no gross geometric changes.

The present invention changes the direction of ultrasonic longitudinal vibrations without generating parasitic motion, heat or noise, or resulting in early failures of instruments incorporating the present invention, and can produce a tighter radius of curvature than is typically accepted as being possible in the prior art, and has potential applications in articulated ultrasonic instruments.

In accordance with the teachings herein, the present invention provides a waveguide and a method for redirecting substantially longitudinal ultrasonic vibrations along a first axis to substantially longitudinal motion along a second axis inclined at an angle relative to the first axis. First and second half-wave sections are provided, wherein each half-wave section has a straight portion, a curved portion with an end tip, and a balancing region. The half-wave sections are joined at the tips of their curved portions, and the ultrasonic vibrations at the tip of the curved portion of the first half-wave section are substantially identical in magnitude and direction to the vibrations at the tip of the curved portion of the second half-wave section.

In greater detail, the direction of the ultrasonic vibrations at the tip of each respective curved portion of each section are preferably tangential to the curve. The radius of each of the curved portions of the first and second half-wave sections can extend over a subtended angle up to the maximum possible angle of 180 degrees.

In different embodiments, two identical first and second half-wave sections are joined at the tips of their curved portions. In alternative embodiments, the first and second half-wave sections have different geometries. In one embodiment, ultrasonic vibrations produced by an ultrasonic generator are introduced into one end of the waveguide, and an end-effector cutting element is positioned at a second end of the waveguide.

Each half-wave section is designed such that the magnitude of the ultrasonic vibrations, from one end of each half-wave section to the other end of each half-wave section, has one-half of the wavelength throughout the half-wave section. The amplitudes of the ultrasonic vibrations are a maximum at one end of each half-wave section, decrease to a nodal point near the center of each half-wave section and increase again to a maximum at the tip at the opposite end of each half-wave section.

In several embodiments, the first and second half-wave sections are integrally joined into one continuous piece at the tips of their curved portions. In alternative embodiments, the first and second half-wave sections are compressively loaded against each other at the tips of their curved portions and are not integrally connected together. Moreover, the first and second half-wave sections can be rotatable relative to each other, such that the effective angle between input and output portions of the waveguide can be continuously varied.

BRIEF DESCRIPTION OF THE DRAWINGS

The foregoing objects and advantages of the present invention for method and waveguides for changing the direction of longitudinal vibrations may be more readily understood by one skilled in the art with reference being had to the following detailed description of several preferred embodiments thereof, taken in conjunction with the accompanying drawings wherein like elements are designated by identical reference numerals throughout the several views, and in which:

FIG. 9 illustrates an articulatable embodiment of the waveguide of FIG. 2, shown in the straight position in FIG. 9, while FIG. 2 illustrates the greatest angle of articulation, with any angle of articulation inbetween being possible.

DETAILED DESCRIPTION OF THE DRAWINGS

Referring to the drawings in detail, FIGS. 1 through 4 illustrate several different embodiments of curved waveguides constructed pursuant to the teachings of the present invention. Each curved waveguide comprises first and second connected half-wave sections 1, 1, each having a straight portion 2, a curved portion 3, and a balancing region 4, all forming a subtended angle 5. The waveguide has a substantially circular cross section at each straight portion 2, and a substantially flattened cross section at each curved portion 3, as illustrated more clearly by the embodiment shown in FIGS. 6 and 7. Each balancing region 4 includes two curved undercut sections 6, one on each opposite side of the straight portion 2 adjacent to the curved portion 3. Material removed from (or added to) each undercut section 6 helps to balance the piece in a manner as disclosed and taught in U.S. Ser. Nos. 106,661 and 106,686. Each half-wave section, 1, 1 ends in a tip 7 at the end of the curved portion. The half-wave sections 1, 1 are integrally or compressively joined at 8 at the tips to form the curved waveguide.

Each half-wave section 1 is designed such that, at the desired operating frequency, the tips 7, 7 have a vibratory response substantially identical in magnitude and direction. FIGS. 5 and 8 are vector plots of the vibrations of respectively the embodiments of FIGS. 4 and 6–7, and illustrate the magnitude and direction of vibrations at different portions of the waveguide, and show the nearly identical magnitude and direction of the vibrations of the waveguide on either side of the tips 7, 7.

Each half-wave section 1 is designed so that the magnitude of vibration, from one end of the half-wave section to the other end thereof at any given point in time, has one-half of the wavelength throughout the section 1. Preferably, in one embodiment of the invention, the amplitude of the vibrations is at a maximum at one end of each section 1, decreases to a nodal point near the center of the half-wave section 1, and increases again to a maximum at the tip at the opposite end thereof. The amplitude of vibrations at the tip 7 is generally opposite in phase to the amplitude at the opposite end of the half-wave section 1, thereby providing the half-wave form.

Figure 1:
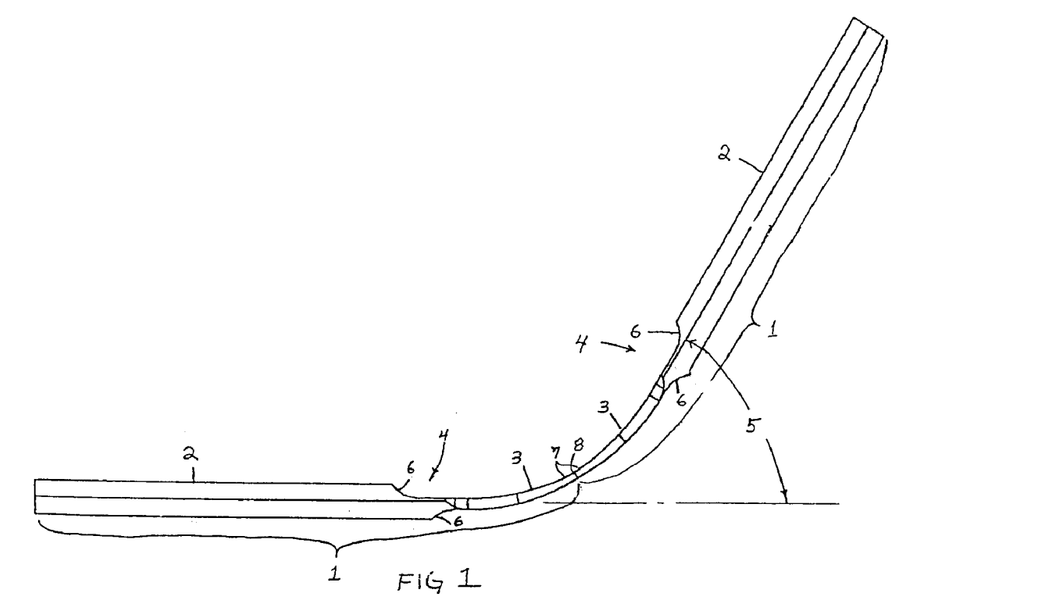
FIG. 1 illustrates a first embodiment of a curved waveguide having a bend radius of 0.795 inches and a bend angle of 60 degrees.
Figure 2:
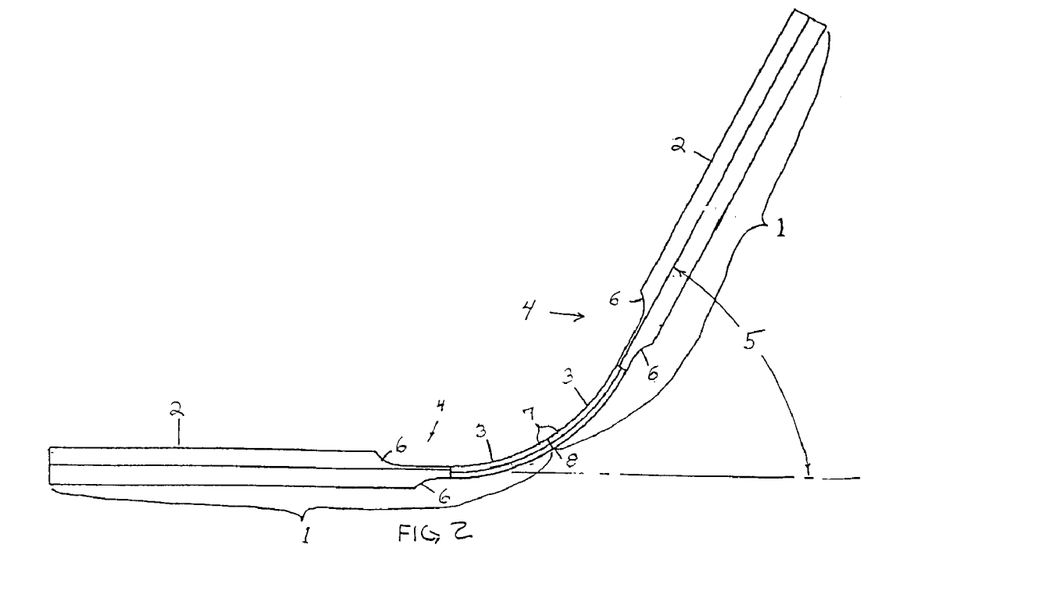
FIG. 2 illustrates a second embodiment of a refined version of the curved waveguide shown in FIG. 1 having a bend radius of 0.750 inches and a bend angle of 62 degrees.
Figure 3:
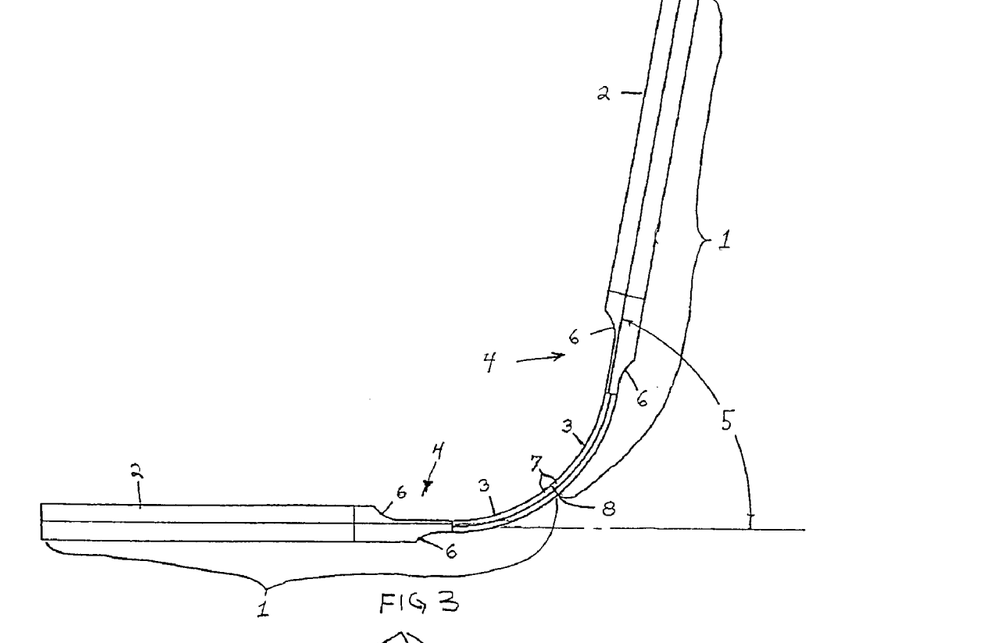
FIG. 3 illustrates a third embodiment of a modified version of the curved waveguide of FIG. 2 having a bend radius of 0.6 inches and a bend angle of 80 degrees.
Figure 4:
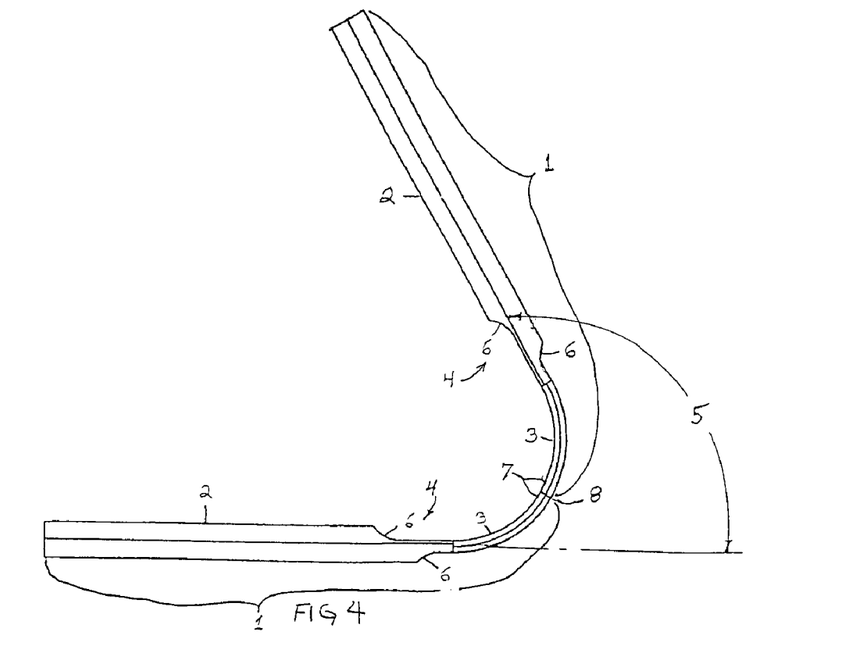
FIG. 4 illustrates a fourth embodiment of a curved waveguide similar to the embodiments of FIGS. 2 and 3 and having a bend radius of 0.39 inches and a bend angle of 120 degrees.
Figures 5, 8:
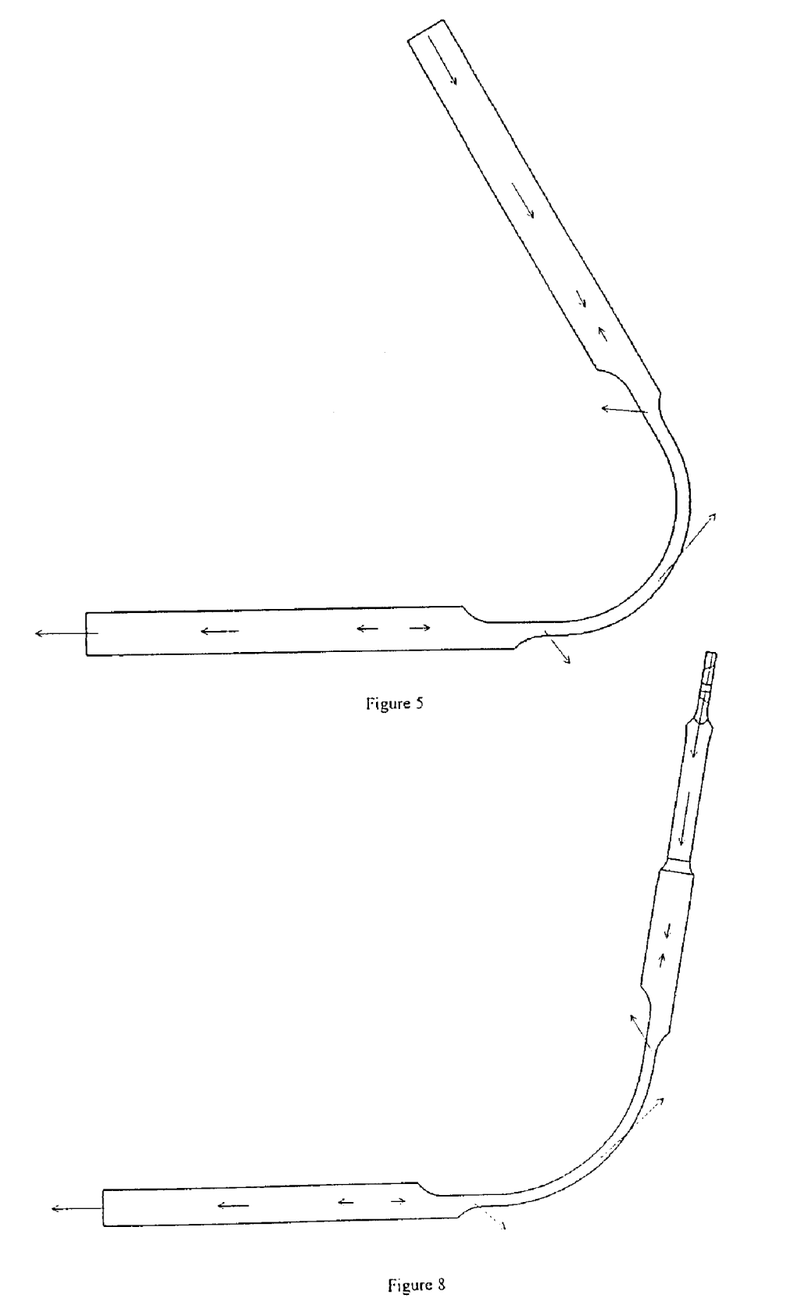
FIG. 5 is a vector plot of the vibrations of the embodiment of FIG. 4 and illustrates longitudinal motion without transverse motion at the ends of the curved waveguide, and also illustrates allowed transverse motion at the bend section.
FIG. 8 is a vector plot of the vibrations of the embodiment of FIGS. 6 and 7.

The four designs of the embodiments of FIGS. 2 through 4 demonstrate a steadily increasing subtended angle 5 and a decreasing radius of curvature of the curved section 3. The embodiment of FIG. 4 demonstrates that a bend angle of 120 degrees and a bend radius of 0.39 inches are achievable with the current invention. In this particular embodiment of the invention, designed for use with titanium at a frequency of 55.5 kHz, the wavelength is approximately 3.4 inches. Hence, useful vibration is redirected at a large angle 5 using a very small radius of curvature, well below the transmitted wavelength of the ultrasonic instrument.

Figure 6:
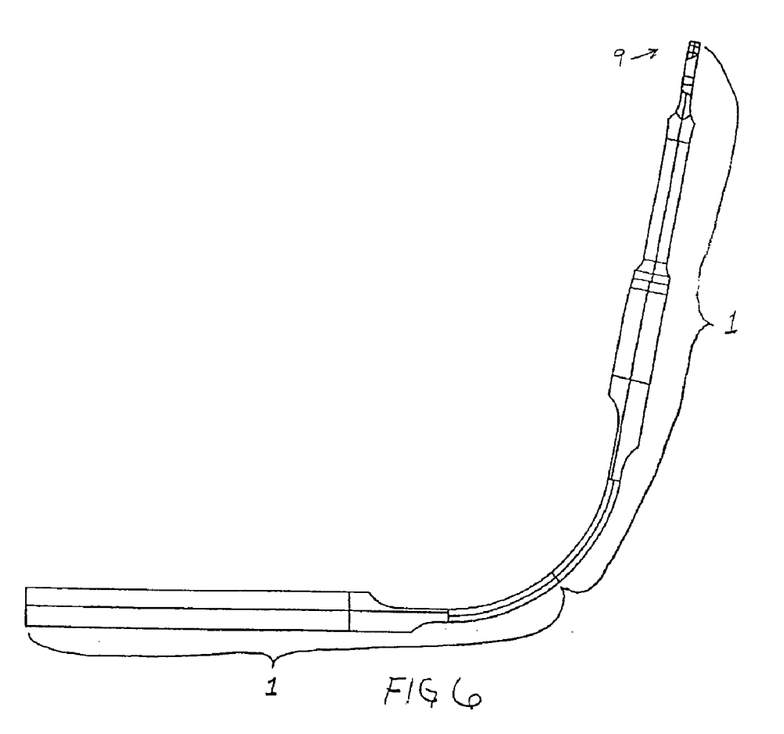
FIG. 6 illustrates a modification of the embodiment of FIG. 3 in a curved waveguide having a hook end-effector.

Ultrasonic energy is introduced at one end of the waveguide, causing ultrasonic vibration therein which proceeds down the waveguide and through the joined tips 7, 7 of each half-section 1,1. The energy causes ultrasonic vibratory motion at the other end of the waveguide which can perform useful work. Energy passes through the joined tips with negligible loss. As shown in FIGS. 5 and 8, the direction of the vibration is substantially parallel to the waveguide at each end 7 of each straight portion 2, but is not necessarily tangential to the curve of the waveguide at each curved section 3. The parallel ultrasonic vibrations at each end 7 allows the waveguide to perform useful work. For example, a cutting element 9, as shown in FIG. 6, can be placed at one end of the waveguide, to perform surgery.

Figure 7:
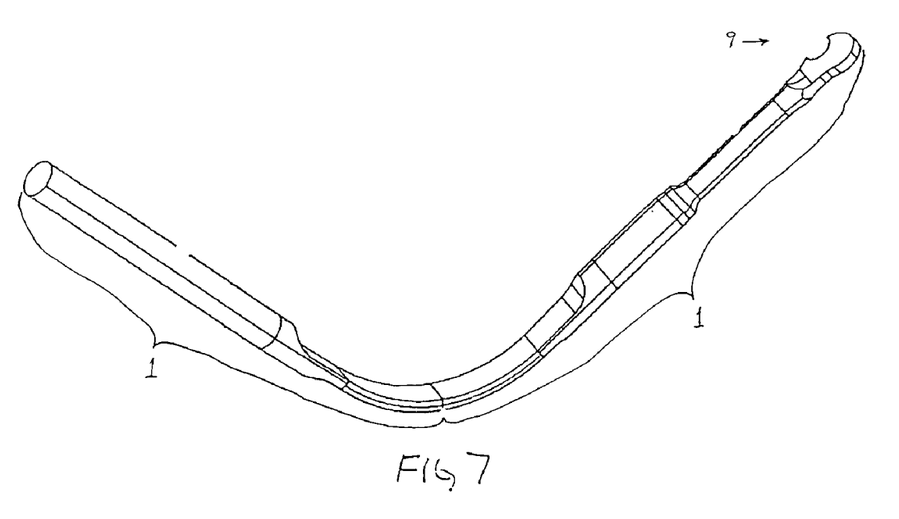
FIG. 7 illustrates a rotated view of the embodiment of FIG. 6.

The half-wave sections 1,1 do not need to be identical. FIGS. 6, 7 and 8 illustrate a waveguide created from half-wave sections 1,1 which are not identical in appearance. Nonidentical sections allow the joining of useful sections at the ends of sections that are most advantageous for connection to the ultrasonic transmitters. Placing a cutting section 9 at one end of a half-wave section 1 suitable to be driven by an ultrasonic transmitter allows the invention to perform useful work around a bend angle.

Figure 9:
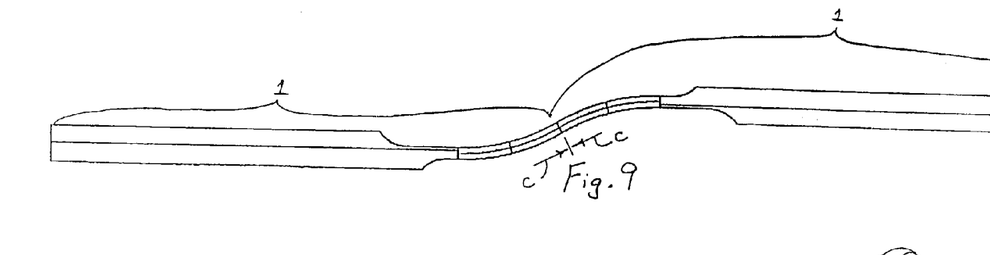

FIG. 9 illustrates an articulatable embodiment of the waveguide of FIG. 2, shown in the straight position in FIG. 9, while FIG. 2 illustrates a greater angle of articulation, with any angle of articulation up to the maximum possible angle of 180 degrees being possible.

Further embodiments of the invention can use balanced first and second half-wave sections 1, 1 as described herein, wherein the first and second sections are compressively loaded against each other, as indicated by compression arrows C in FIG. 9, and are not rigidly connected together, achieving the same effect as a solid member by using methods of loading as described in U.S. Pat. No. 6,063,098. By rotating the sections 1, 1 relative to one another about an axis perpendicular to the mating surface and passing perpendicularly through the mating surface, the effective angle between the input and the output of the sections 1, 1 of the waveguide can be continuously varied.

Each half-wave section 1,1 is preferably designed according to the disclosures and teachings of U.S. Ser. Nos. 106,661 and 106,686, filed on Jun. 29, 1998, and commonly assigned herewith.

The following description of FIGS. 10 through 15 is incorporated from the disclosures of U.S. Ser. Nos. 106,661 and 106,686 for completeness herein, but the disclosures of U.S. Ser. Nos. 106,661 and 106,686, which are expressly incorporated by reference herein, should be consulted for a fuller explanation of the design methodology of each half-wave section 1,1.

Figure 10:
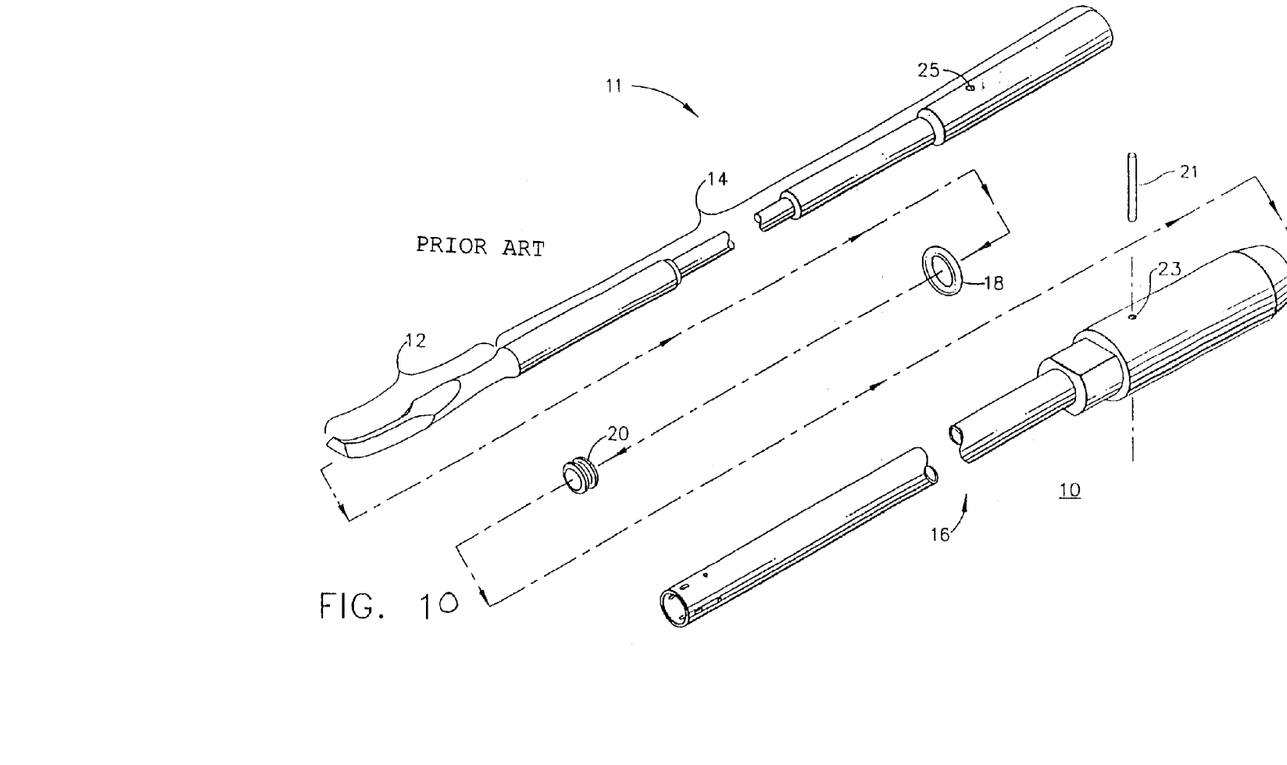
FIG. 10 is an exploded perspective view of a prior art ultrasonic surgical instrument according to U.S. Ser. Nos. 106,661 and 106,686.

FIG. 10 is an exploded perspective view of an ultrasonic surgical instrument 10 incorporating a half wave section according to U.S. Ser. Nos. 106,661 and 106,686. In FIG. 10, ultrasonic end-effector 12 is mechanically coupled to ultrasonic transmission waveguide 14 to form ultrasonic transmission assembly 11. Ultrasonic transmission waveguide 14 is positioned in outer sheath 16 by mounting O-ring 18 and sealing ring 20. One or more additional dampers or support members (not shown) may also be included along ultrasonic transmission waveguide 14. Ultrasonic transmission waveguide 14 is affixed to outer sheath 16 by mounting pin 21, which passes through mounting holes 23 in outer sheath 16 and mounting slot 25 in transmission waveguide 14.

Figure 11:
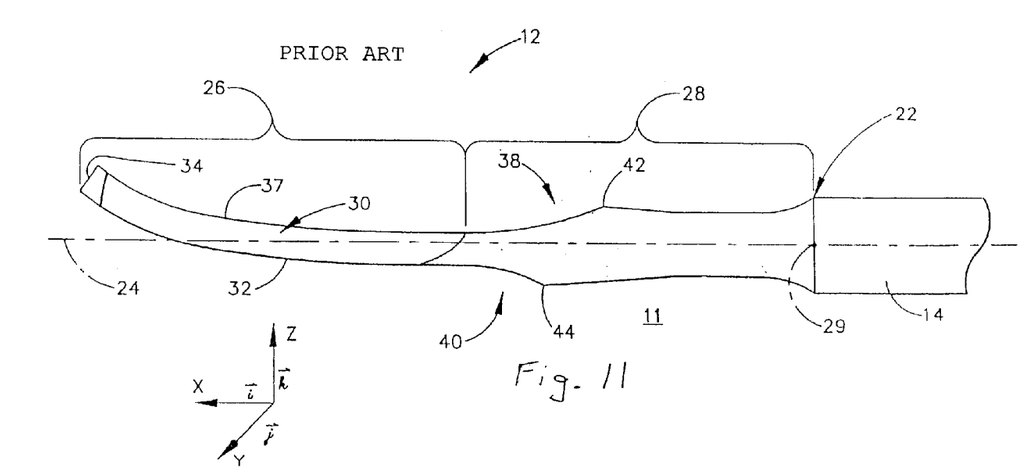
FIG. 11 is a side view of the distal end of the prior art ultrasonic transmission assembly pursuant to U.S. Ser. Nos. 106,661 and 106,686.

FIG. 11 is a side view of the distal end of ultrasonic transmission assembly 11, including end-effector 12. FIG. 11 further includes an ordinate system in which: the x-axis lies along central axis 24 of ultrasonic transmission waveguide 14 while the y-axis is the axis of curvature of treatment region 26. In the embodiments of the invention described therein, end-effector 12 is affixed to the distal end of transmission waveguide 14 at balance node 22. Central axis 24 of transmission waveguide 14 extends from the proximal end of transmission waveguide 14 to the distal end of transmission waveguide 14. Transmission waveguide 14 is symmetrical about central axis 24. End-effector 12 includes treatment region 26, which is located at the distal end of end-effector 12 and balance region 28 which is located between treatment region 26 and balance node 22. Treatment region 26, being curved, includes two surfaces, a concave top surface 30 and a convex bottom surface 32. Convex bottom surface 32 is substantially planar or flat along the y-axis of the blade. Treatment region 26 further includes rounded tip 34. In the illustrated embodiment, balance region 28 includes a first cutout 38 and a second cutout 40 which act as asymmetric balance features. First cutout 38 extending from the proximal end of concave surface 30 to a first predetermined point 42 which is distal to balance node 22. Second cutout 40 extends from the proximal end of convex surface 32 to a second predetermined point 44 which is distal to point 42 and balance node 22.

Figure 12:
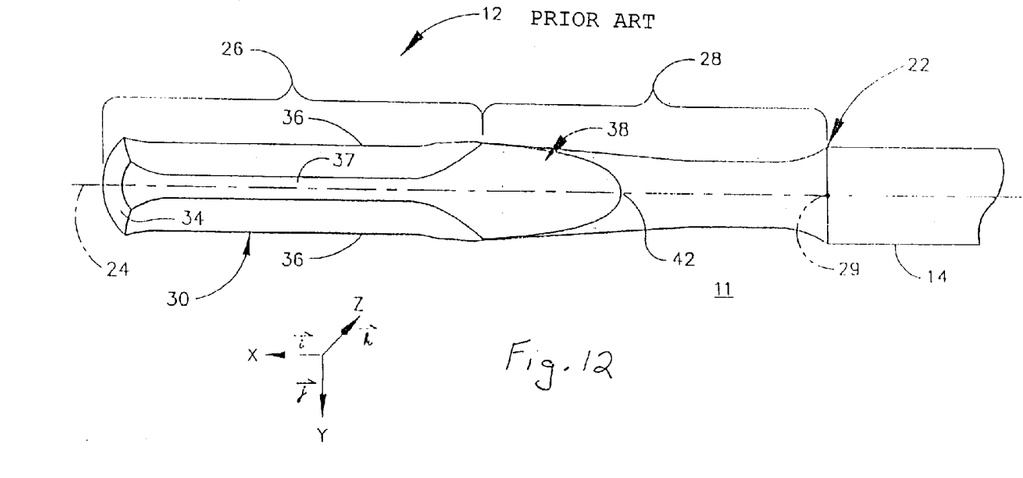
FIG. 12 is a top view of the distal end of the prior art ultrasonic transmission assembly according to U.S. Ser. Nos. 106,661 and 106,686.

FIG. 12 is a top view of the distal end of ultrasonic transmission assembly 11, including end-effector 12. In FIG. 12, blade edges 36 are positioned on both sides of treatment region 26 and extend from the proximal end of treatment region 26 to rounded tip 34. The intersection of concave surface 30 and convex surface 32 form blade edges 36. Central ridge 37 runs from the distal end of balance region 28 to rounded tip 34 along the center of treatment region 26. Central ridge 37 forms a portion of concave top surface 30. Central ridge 37 adds strength, stiffness and rigidity to treatment region 26 by giving treatment region 26 a substantially trapezoidal cross-section.

Figure 13:
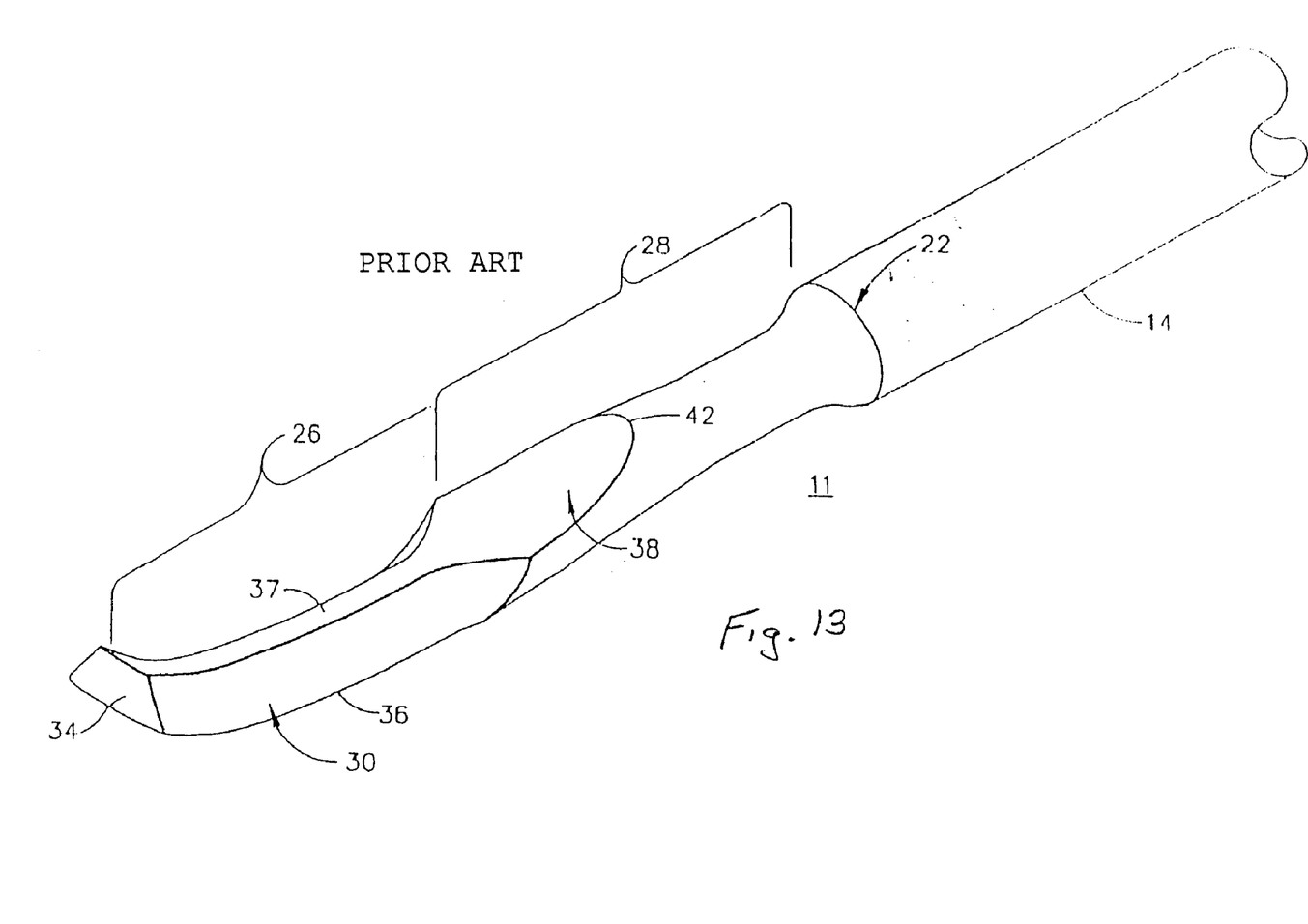
FIG. 13 is a perspective view of the distal end of a prior art alternate embodiment of an ultrasonic transmission assembly pursuant to U.S. Ser. Nos. 106,661 and 106,686.
Figure 14:
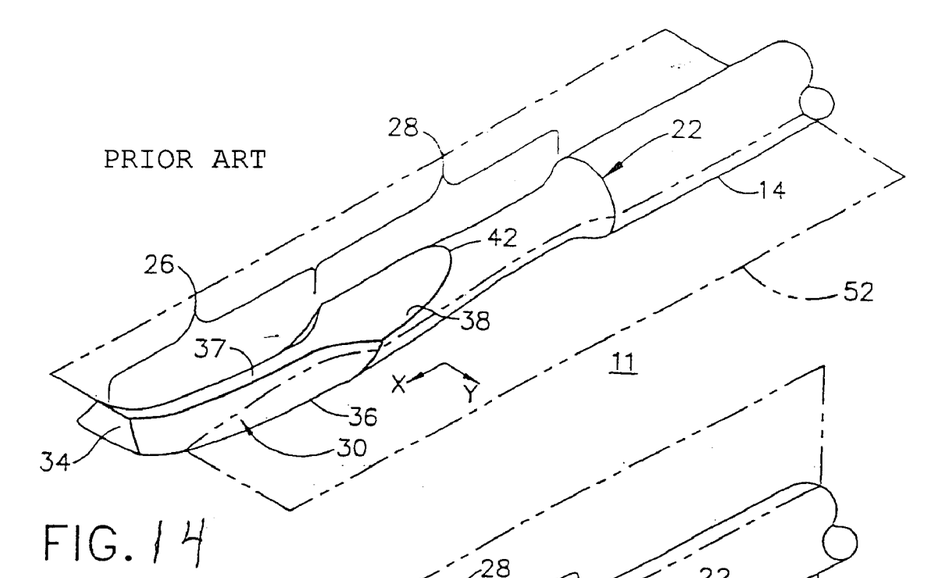
FIG. 14 is a perspective view of the distal end of the prior art ultrasonic transmission assembly shown in FIG. 13 with a phantom x,y plane drawn through the center of the ultrasonic transmission waveguide.

FIG. 13 is a perspective view of the distal end of an embodiment of an ultrasonic transmission assembly 11. FIG. 14 is a perspective view of the distal end of ultrasonic transmission assembly 11 of the embodiment shown in FIG. 13 with a phantom x,y plane 52 drawn through the center of ultrasonic transmission waveguide 14. In FIG. 14, phantom x,y plane 52 passes through central axis 24. Since treatment region 26 curves away from x,y plane 52, end-effector 12 is not symmetrical about x,y plane 52. Plane 52 may, therefore, be referred to as the plane of asymmetry for end-effector 12.

Figure 15:
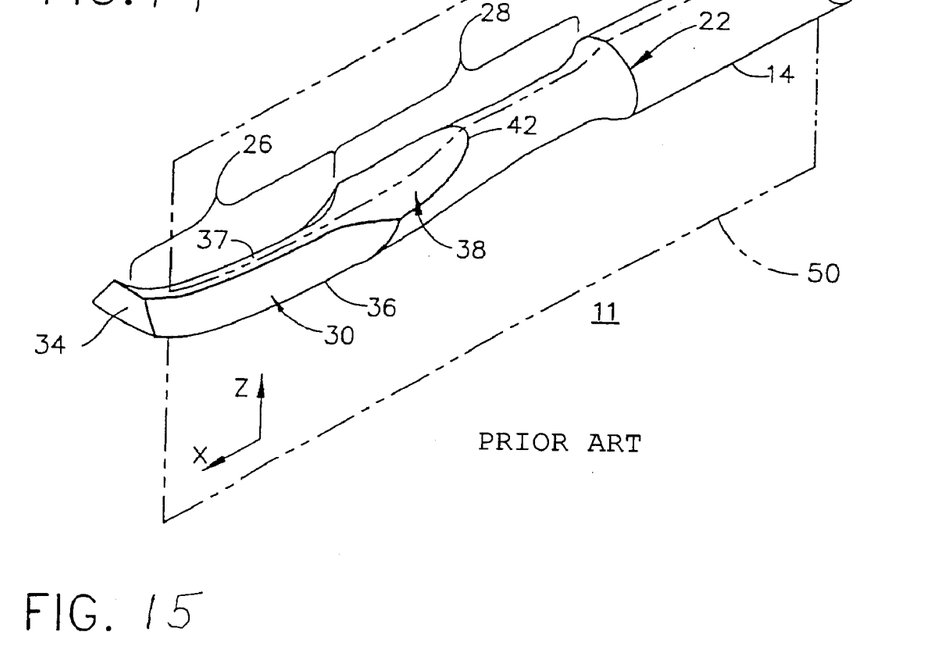
FIG. 15 is a perspective view of the distal end of the prior art ultrasonic transmission assembly shown in FIG. 13 with a phantom x,z plane drawn through the center of the ultrasonic transmission waveguide.

FIG. 15 is a perspective view of the distal end of the ultrasonic transmission assembly 11 of the embodiment shown in FIG. 13 with a phantom x,z plane 50 drawn through the center of ultrasonic transmission waveguide 14. In FIG. 15, phantom x,z plane 50 passes through central axis 24 at an angle at 90° to x,y plane 52. End-effector 12 is substantially symmetrical about x,z plane 50. Plane 50 may, therefore, be referred to as the plane of symmetry for end-effector 12.

Ultrasonic surgical instrument 10 has a treatment region 26 which includes a curved blade designed to cut and coagulate tissue when vibrated at ultrasonic frequencies, such as, for example, fifty-five kilohertz (55 kHz). Treatment region 26 is curved to provide the surgeon with better access and visibility when using ultrasonic instrument 10. As illustrated in FIGS. 14–15, curved treatment region 26 is symmetrical about x,z plane 50 but is not symmetrical about x,y plane 52. When treatment region 26 is vibrated at an appropriate ultrasonic frequency to facilitate cutting and coagulation, the asymmetrical shape of treatment region 26 will tend to induce undesirable forces, including torque, which are transmitted back to transmission waveguide 14 and induce undesirable transverse vibrations in transmission waveguide 14.

It is known that these undesirable transverse vibrations may be minimized and the end-effector balanced by designing the end-effector such that the center of mass at any point along the end-effector is positioned on or very near the central axis of the transmission waveguide. However, where the asymmetry (e.g. the curve of treatment region 26), causes the center of mass to diverge substantially from a line extending from the central axis of the transmission waveguide and the addition of balance features within the treatment region is undesirable, the blade must be balanced using an alternative method.

According to U.S. Ser. Nos. 106,661 and 106,686, the end-effector 12 is balanced by reducing or eliminating the torque induced in end-effector 12 proximal to treatment region 26 as a result of including functional asymmetrical features in treatment region 26. A convenient physical point of reference at the proximal end of end-effector 12 is balance node 22. It should be noted that balance node 22 may be any node of longitudinal vibration along transmission waveguide 14 and is not necessarily the most distal vibratory node. Nodes of longitudinal vibration occur at half wavelength intervals along the transmission waveguide, wherein the wavelength of interest is the wavelength of the frequency at which the ultrasonic end-effector is driven (e.g. 55 kHz). In the embodiment illustrated in FIG. 12, the asymmetric functional features comprise curved treatment region 26 having rounded tip 34. A feature is asymmetric when its cross-section is not symmetric with respect to waveguide central axis 24. A feature is symmetric when the cross-section is symmetric with respect to waveguide central axis 24. That is, a feature is symmetric when a chord through a cross-section of the portion of the end-effector, which includes the feature, is bisected by central axis 24.

According to U.S. Ser. Nos. 106,661 and 106,686, a balance region 28 (equivalent to balance regions 4 of FIGS. 1–4, 6, 7 and 9) is included in end-effector 12 and end-effector 12 is balanced by positioning at least two asymmetric balance features in balance region 28 between the proximal end of treatment region 26 and balance node 22. The size, shape and position of the asymmetric balance features included in balance region 28 are selected to reduce the torque at a balance point 29 to zero or as close to zero as possible. Balance point 29 is on central axis 24 positioned at, for example, balance node 22. The degree to which torque is reduced will depend upon particular design and manufacturing constraints. Thus, by appropriately arranging asymmetric balance features in balance region 28, the torque induced by the asymmetric functional features in treatment region 26 may be canceled by the torque induced by the asymmetric balance features. With the summation of torque distal to end-effector 12 minimized, the transverse vibration in transmission waveguide 14 will be substantially reduced and may be reduced to approximately zero.

In order to determine whether an asymmetric end-effector has been properly balanced, it may be appropriate to measure the torque induced in transmission waveguide 14. The relative magnitude of the torque induced in transmission waveguide 14 may be estimated by taking the ratio of the peak lateral displacement, less Poisson's swelling (also referred to as longitudinal node swelling), at any transverse vibratory antinode of the transmission waveguide to the peak longitudinal displacement at any longitudinal vibratory antinode of the transmission waveguide. The closer the ratio is to zero, the less transverse vibration is being induced in the waveguide. Thus, the ratio of peak lateral displacement to peak longitudinal displacement may be referred to as the "balance ratio". In one embodiment, a blade would be considered balanced if the balance ratio of peak lateral displacement to peak longitudinal displacement is 1:10 or less. More particularly, using the techniques described herein, it may be possible to achieve balance ratios of 1:200 or less.

An asymmetric feature is a feature of the end-effector wherein the center of mass of the feature is off a line extending from the central axis of the transmission waveguide. In an end-effector having a symmetrical orientation and an asymmetrical orientation, such as the end-effector illustrated in the Figures, all of the asymmetric features are in a plane parallel to the plane of symmetry.

The mass and shape of the asymmetric balance features introduced into balance region 26 are determined by a number of factors. The torque induced at balance point 29 is equal to the integral over volume of the cross product of the vector acceleration at each point on the end-effector with a position vector multiplied by a density scaler. The density scaler is a function which represents the density of the end-effector at each point on the end-effector. Expressing that equation mathematically, the torque ($\overline{T}$) at balance point 29 is $$\int_{x_0}^{x_1}\int_{y_0}^{y_1}\int_{z_0}^{z_1}\overline{A}(x,y,z)x\overline{o}(x,y,z)\rho(x,y,z)dzdydx, \qquad (1)$$

where:

$x_0$, $y_0$, $z_0$ are located in the plane x=0 at balance point 29;

$x_1$, $y_1$, $z_1$, are located in a plane tangential to the distal tip of end-effector 12 and, with $x_0$, $y_0$, and $z_0$, define a region which encloses end-effector 12;

$\overline{A}$ (x,y,z) is the acceleration of the blade at any point (x,y,z);

$\overline{o}$ (x,y,z) is a vector indicative of the position of the point (x,y,z) with respect to balance point 29;

and $\rho$ (x,y,z) is the density of the blade at any point (x,y,z).

Therefore, in a balanced end-effector designed according to U.S. Ser. Nos. 106,661 and 106,686, an end-effector 12 is first designed which incorporates one or more beneficial asymmetries in treatment region 26 (e.g. curved blade edges 36). A balance node point is then selected at a conventional vibratory node along waveguide 14. Normally the balance node point will be the most distal vibratory node on waveguide 14. A symmetrical (e.g. cylindrical) balance region 28 is then incorporated into end-effector 12. In the illustrated embodiments, balance region 28 extends from balance node 22 to the proximal end of treatment region 26. Normally the proximal end of treatment region 26 will correspond with the proximal end of the proximal most beneficial asymmetry. For example, in the embodiment of the invention illustrated in FIG. 11, the proximal end of treatment region 26 corresponds to the proximal end of curved blade edge 36. Once the appropriate beneficial asymmetries have been designed into the end-effector, the torque induced at balance point 29 by the end-effector design, including beneficial asymmetries may be calculated using Equation (1) of U.S. Ser. Nos. 106,661 and 106,686.

U.S. Ser. Nos. 106,661 and 106,686 also disclose and discuss, in addition to the theoretical methodologies described therein, several empirical methods for designing each half-wave section 1,1.

While several embodiments and variations of the present invention for a method and waveguides for changing the direction of longitudinal vibrations are described in detail herein, it should be apparent that the disclosure and teachings of the present invention will suggest many alternative designs to those skilled in the art.

What is claimed is:

1. A waveguide for redirecting substantially longitudinal ultrasonic vibrations along a first axis to substantially longitudinal motion along a second axis inclined at an angle relative to the first axis, the waveguide comprising;

first and second half-wave sections, each half-wave section including a straight portion, a balancing region, and a curved portion with an end tip located in series along the length of the half-wave section, the straight portion of the first half-wave section extending along the first axis, and the curved portion of the first half-wave section curving from the first axis to the curved portion of the second half-wave section;

the straight portion of the second half-wave section extending along the second axis, and the curved portion of the second half-wave section curving from the curved portion of the first half-section to the second axis;

the half-wave sections being joined at the tips of their curved portions, and wherein the ultrasonic vibrations at the tip of the curved portion of the first half-wave section are substantially identical in magnitude and direction to the vibrations at the tip of the curved portion of the second half-wave section.

2. The waveguide as claimed in claim 1, wherein the direction of the ultrasonic vibrations at the tip of each respective curved portion of each section are tangential to the curve.

3. The waveguide as claimed in claim 1, comprising two identical first and second half-wave sections joined at the tips of their curved portions.

4. The waveguide as claimed in claim 1, wherein the first and second half-wave sections have different geometries.

5. The waveguide as claimed in claim 1, wherein the radius of each of the curved portions of the first and second half-wave sections extends over a subtended angle up to the maximum possible angle of 180 degrees.

6. The waveguide as claimed in claim 1, wherein each half-wave section is designed such that the magnitude of the ultrasonic vibrations, from one end of each half-wave section to the other end of each half-wave section, has one-half of the wavelength throughout the half-wave section, and the amplitudes of the ultrasonic vibrations are a maximum at one end of each half-wave section, decrease to a nodal point near the center of each half-wave section and increase again to a maximum at the tip at the opposite end of each half-wave section.

7. The waveguide as claimed in claim 1, wherein ultrasonic vibrations produced by an ultrasonic generator are introduced into one end of the waveguide, and an end-effector cutting element is positioned at a second end of the waveguide.

8. The waveguide as claimed in claim 1, wherein the first and second half-wave sections are integrally joined into one continuous piece at the tips of their curved portions.

9. The waveguide as claimed in claim 1, wherein the first and second half-wave sections are compressively loaded against each other at the tips of their curved portions and are not integrally connected together.

10. The waveguide as claimed in claim 9, wherein the first and second half-wave sections are rotatable relative to each other, such that the effective angle between input and output portions of the waveguide can be continuously varied.

11. A method for redirecting substantially longitudinal ultrasonic vibrations along a first axis to substantially longitudinal motion along a second axis inclined at an angle relative to the first axis, the method comprising providing first and second half-wave sections, each half-wave section including a straight portion, a balancing region, and a curved portion with an end tip located in series along the length of the half-wave section, the straight portion of the first half-wave section extending along the first axis, and the curved portion of the first half-wave section curving from the first axis to the curved portion of the second half-wave section;

the straight portion of the second half-wave section extending along the second axis, and the curved portion of the second half-wave section curving from the curved portion of the first half-section to the second axis;

joining together the half-wave sections at the tips of their curved portions, and providing ultrasonic vibrations at the tip of the curved portion of the first half-wave section which are substantially identical in magnitude and direction to the vibrations at the tip of the curved portion of the second half-wave section.

12. The method as claimed in claim 11, comprising providing ultrasonic vibrations at the tip of each respective curved portion of each section which are tangential to the curve.

13. The method as claimed in claim 11, comprising providing two identical first and second half-wave sections joined at the tips of their curved portions.

14. The method as claimed in claim 11, comprising providing first and second half-wave sections which have different geometries.

15. The method as claimed in claim 11, comprising providing a radius of each of the curved portions of the first and second half-wave sections which extends over a subtended angle up to the maximum possible angle of 180 degrees.

16. The method as claimed in claim 11, comprising designing each half-wave section is designed such that the magnitude of the ultrasonic vibrations, from one end of each half-wave section to the other end of each half-wave section, has one-half of the wavelength throughout the half-wave section, and the amplitudes of the ultrasonic vibrations are a maximum at one end of each half-wave section, decrease to a nodal point near the center of each half-wave section and increase again to a maximum at the tip at the opposite end of each half-wave section.

17. The method as claimed in claim 11, comprising introducing ultrasonic vibrations produced by an ultrasonic generator into one end of the waveguide, and providing an end-effector cutting element at a second end of the waveguide.

18. The method as claimed in claim 11, comprising integrally joining the first and second half-wave sections into one continuous piece at the tips of their curved portions.

19. The method as claimed in claim 11, comprising compressively loading the first and second half-wave sections against each other at the tips of their curved portions, which are not integrally connected together.

20. The method as claimed in claim 19, comprising rotating the first and second half-wave sections relative to each other, such that the effective angle between input and output portions of the waveguide can be continuously varied.

* * * * *